United States Patent
Cannata et al.

[11] Patent Number: 5,859,245
[45] Date of Patent: Jan. 12, 1999

[54] PROCESS FOR THE PRODUCTION OF THE FORM I OF THE ANHYDROUS TERAZOSIN MONOHYDROCHLORIDE

[75] Inventors: Vincenzo Cannata, Borgo Nuovo di Pontecchio Marconi; Tiziano Ferrario, Ceriano Laghetto; Barbara Galbiati, Milan, all of Italy

[73] Assignee: Alfa Chemicals Italiana S.r.l., Bergamo, Italy

[21] Appl. No.: 954,708

[22] Filed: Oct. 20, 1997

[30] Foreign Application Priority Data

Nov. 29, 1996 [IT] Italy ................................. BO96A0611

[51] Int. Cl.$^6$ ................................. C07D 239/84
[52] U.S. Cl. ................................. 544/291; 544/284; 544/295
[58] Field of Search ................................. 544/284, 293, 544/291

[56] References Cited

U.S. PATENT DOCUMENTS

| | | | |
|---|---|---|---|
| 4,026,894 | 5/1977 | Winn et al. | 544/291 |
| 4,251,532 | 2/1981 | Roteman | 544/291 |
| 5,212,176 | 5/1993 | Kyncl et al. | 544/291 |
| 5,294,615 | 3/1994 | Meyer et al. | 544/291 |
| 5,412,095 | 5/1995 | Morley et al. | 544/291 |

*Primary Examiner*—Yogendra N. Gupta
*Attorney, Agent, or Firm*—Bucknam and Archer

[57] ABSTRACT

The process for the production of form I of anhydrous terazosin monohydrochloride consists of heating terazosin suspended in a mixture made by methanol and a solvent selected from $C_2$ to $C_6$, straight or branched alcohols, esters of $C_1$–$C_8$ aliphatic carboxylic acids with straight or branched $C_1$ to $C_8$ alcohols, $C_3$ to $C_8$ aliphatic ketones, $C_4$ to $C_8$ straight branched or cyclic aliphatic ethers, aliphatic amides and aliphatic nitriles with a methanol solution of hydrochloric acid.

3 Claims, 3 Drawing Sheets

PROCESS FOR THE PRODUCTION OF THE FORM I OF THE ANHYDROUS TERAZOSIN MONOHYDROCHLORIDE

BACKGROUND OF THE INVENTION

The compound 1-(4-amino-6,7-dimethoxy-2-quinazolinyl)-4-(tetrahydro-2-furoyl)piperazine is internationally known under the name of terazosin.

This compound, together with the anhydrous monohydrochloride salt, has been described for the first time in U.S. Pat. No. 4,026,894.

In the subsequent U.S. Pat. No. 4,251,532 a crystalline dihydrate form of terazosin has been described defined more stable than the original anhydrous form. This dihydrate form of the terazosin monohydrochloride is at present marketed all over the world, for instance as HYTRIN® in USA and United Kingdom and as ITRIN® in Italy, for the treatment of the hypertension.

Recently U.S. Pat. No. 5,412,095 has described and claimed new crystalline forms of the terazosin monohydrochloride anhydrous, named FORM II and FORM III, and a new process for producing the original anhydrous monohydrochloride crystalline form described in U.S. Pat. No. 4,026,894 named "a posteriori" FORM I.

DESCRIPTION OF THE INVENTION

Object of the present invention is a process for the production of the 1-(4-amino-6,7-dimethoxy-2-quinazolinyl)-4-(tetrahydro-2-furoyl)piperazine monohydrochloride anhydrous in the crystalline form I described in U.S. Pat. Nos. 4,026,894 and 5,412,095.

The 1-(4-amino-6,7-dimethoxy-2-quinazolinyl)-4-(tetrahydro-2-furoyl)piperazine is suspended in a mixture made by methanol and by a solvent selected from the alcohols, straight or branched, from $C_2$ to $C_6$, the esters of the carboxylic aliphatic acids from $C_1$ to $C_8$ with the alcohols, straight or branched, from $C_1$ to $C_8$, the aliphatic ketones from $C_3$ to $C_8$, the aliphatic ethers, straight, branched or cyclic, from $C_4$ to $C_8$, the aliphatic amides and the aliphatic nitriles and the suspension is heated to a temperature between 50° C. and the boiling temperature under strong stirring.

In a preferred aspect of the invention the solvent is selected from ethanol, isopropanol, n-butanol, n-butyl acetate, acetone, methylisobutylketone and n-dibutylether and the mixture is made by an amount by volume of methanol between 1 and 8 times and by an amount by volume of solvent between 3 and 15 times the weight of the 1-(4-amino-6,7-dimethoxy-2-quinazolinyl)-4-(tetrahydro-2-furoyl)piperazine.

A solution of hydrochloric acid in methanol, containing from 0.95 to 1.00 equivalents of hydrochloric acid in respect of the 1-(4-amino-6,7-dimethoxy-2-quinazolinyl)-4-(tetrahydro-2-furoyl)piperazine, is added to the suspension, under strong stirring, in a period of time between 15 minutes and 2 hours while keeping the temperature between 50° C. and the boiling temperature.

At the end of the addition the suspension is further heated to the boiling temperature for a period of time between 10 minutes and 3 hours and, optionally, the mixture methanol/solvent is partially distilled off.

The suspension is then cooled to 20° C. under nitrogen atmosphere and an amount of hydrochloric acid in methanol between 0.02 and 0.10 equivalents in respect of the 1-(4-amino-6,7-dimethoxy-2-quinazolinyl)-4-(tetrahydro-2-furoyl)piperazine is added under strong stirring. The suspension is kept under strong stirring for a period of time between 10 and 30 minutes and then is filtered. The crystalline solid is washed with the solvent and dried in oven under vacuum at a temperature between 70° C. and 75° C. for a period of time between 12 and 24 hours.

The so obtained pure product has been characterized through three kinds of structural analytic techniques: powder X-ray diffraction, IR spectrum and differential thermal analysis.

The technique of powder X-ray diffraction has been carried out by means of an automatic powder diffractometer Philips model PW1050, controlled by a PW1710 unit, with Bragg-Brentano geometry, by means of monochromatic $CuK_\alpha$ radiation (wavelength 1.54060 Å, 40 kV and 40 mA) with scansion interval 3–40 in 2θ in degrees, angular pitch 0.02 degrees and scansion time 1.25 seconds for angular pitch and at room temperature.

The samples have been dry prepared by light grinding in agate mortar without compression.

BRIEF DESCRIPTION OF THE DRAWINGS

The intensities of the diffracted X rays (counts) in function of the diffraction angle 2θ are reported in the diffractogram of FIG. 1.

The IR spectrum, reported in FIG. 2, has been carried out by means of a Fr-IR Perkin Elmer 6100 spectrophotometer on samples containing 0.3% of product in KBr with registration between 4400 and 600 $cm^{-1}$.

Figure 3:
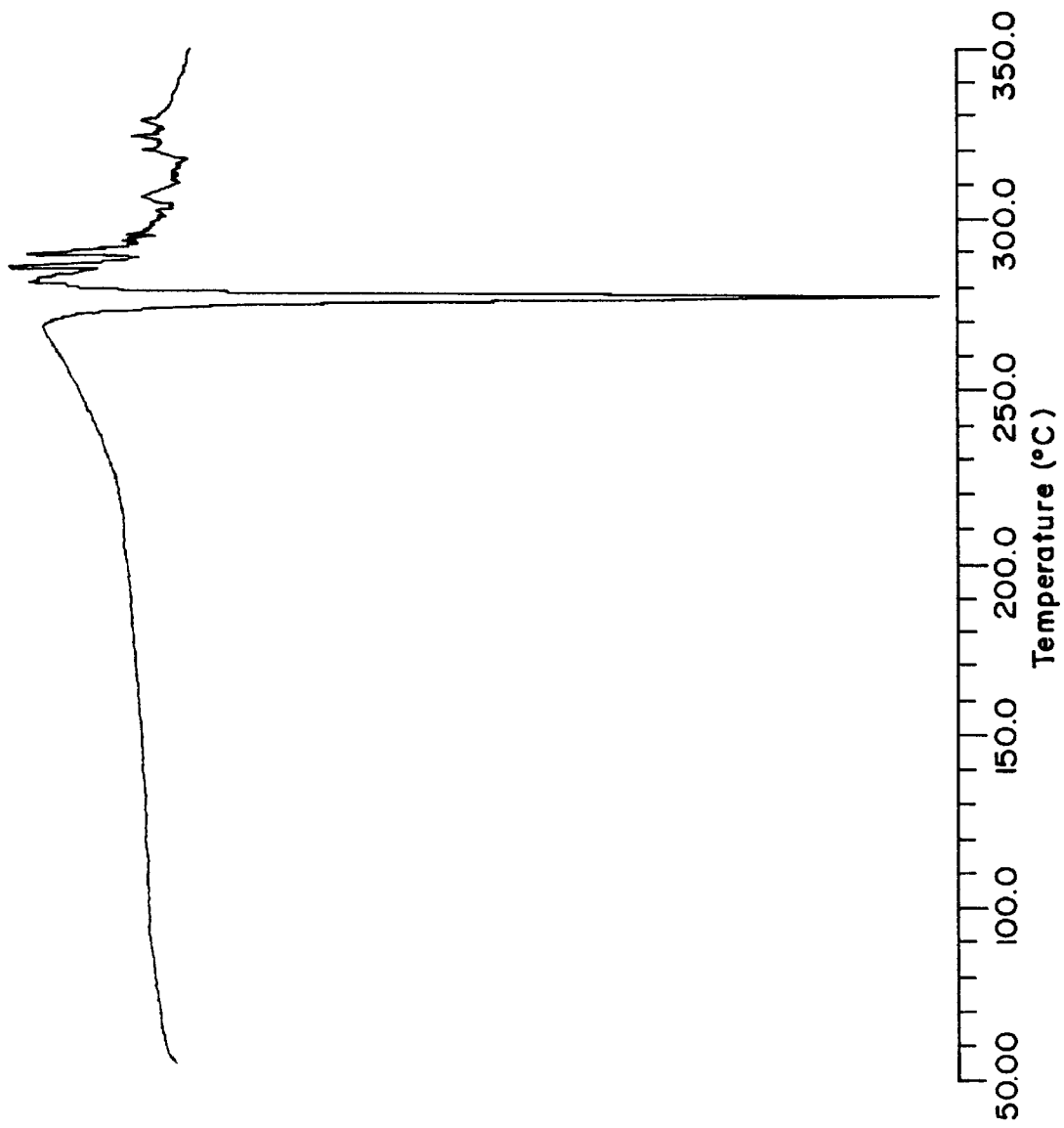

The differential thermal analysis, with the thermogram reported in FIG. 3, has been carried out with an instrument DSC METTLER TA 4000, starting from an initial temperature of 50° C. till a temperature of 350° C. and with a scansion speed equal to 5° C./min. The analysis has been carried out on a holed melting-pot containing an amount of substance between 4 and 6 mg.

This process is much more advantageous than that described in U.S. Pat. No. 5,412,095 as it is carried out in a very simple way as regards the operative conditions and with equipments normally used in the industrial synthesis plants, in a sole step with very high yields, greater than 90%.

On the contrary, the process described in the above mentioned US Patent goes, under strictly anhydrous conditions, through the formation and the isolation of a methanolate hydrochloride intermediate, with yields of about 93%, followed by the subsequent transformation of the methanolate hydrochloride into anhydrous hydrochloride, with yields of about 78%, so that the overall final yield is about 72%.

Therefore the new process is remarkably better than that described in U.S. Pat. No. 5,412,095, both from the manufacture and the cost point of view.

The examples underneath reported have to be considered as a further illustration of the invention and not as an its limitation.

EXAMPLE 1

40 Grams of 1-(4-amino-6,7-dimethoxy-2-quinazolinyl)-4-(tetrahydro-2-furoyl) piperazine are suspended in a mixture made by 160 ml of methanol and 300 ml of n-butyl acetate in a three-necked flask equipped with stirrer and cooling coil and the reaction mixture is heated to the boiling temperature under strong stirring. An amount of 52.7 ml of a 7% (w/v) solution of hydrochloric acid in methanol is added during the period of one hour while keeping the mixture at the boiling temperature.

The reaction mixture is cooled to 20° C. under nitrogen atmosphere 10 minutes after the end of the addition, added with 2.1 ml of 7% (w/v) solution of hydrochloric acid in methanol, kept under stirring for 10 minutes and then filtered. The solid is washed on the filter with 40 ml of n-butyl acetate and dried in oven under vacuum at 70° C. for 12 hours obtaining 41.2 g of product with a yield equal to 94.4%.

Figure 1:
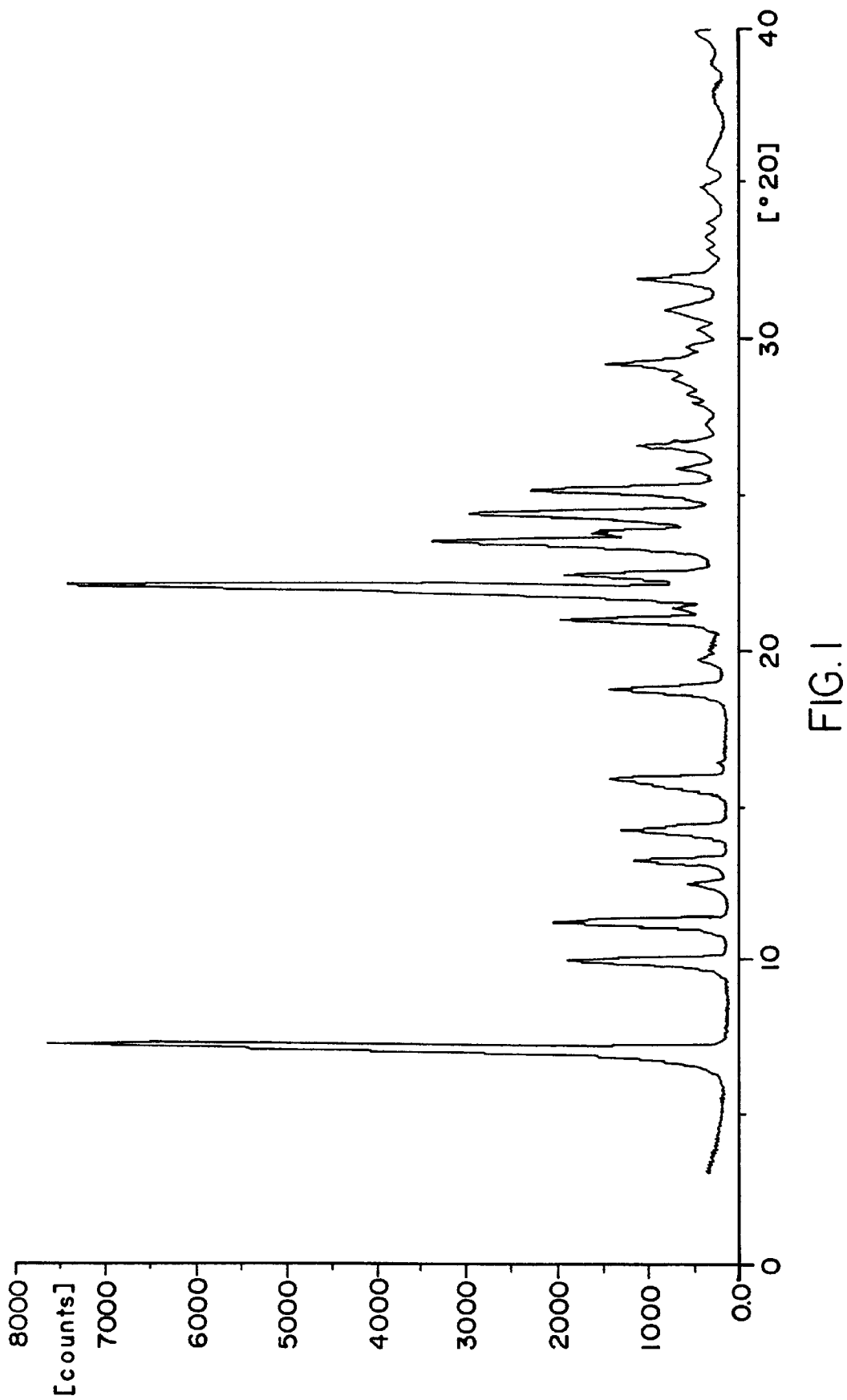
Figure 2:
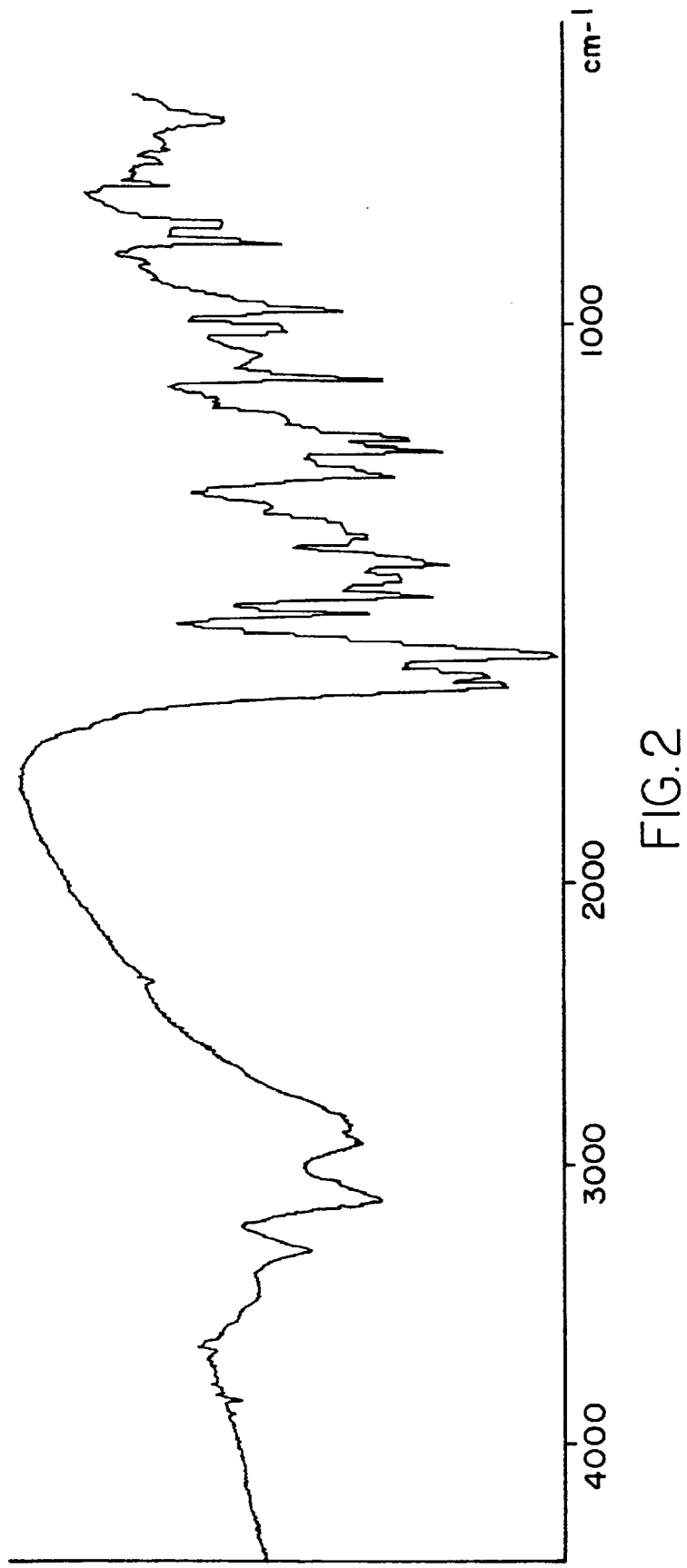

Samples of the product have been submitted to three kinds of structural analytical techniques: powder X-ray diffraction (FIG. 1), IR spectrum (FIG. 2) and differential thermal analysis (FIG. 3). The diffraction angles 2θ more significant, with an approximation of ±0.2°, obtained in the powder X-ray diffraction are as follows: 7.15°; 10.04°; 11.08°; 11.22°; 14.20°; 15.90°; 18.78°; 20.91°; 21.90°; 22.42°; 23.45°; 23.75°; 24.35°; 25.10° and 29.15°.

EXAMPLE 2

20 Grams of 1-(4-amino-6,7-dimethoxy-2-quinazolinyl)-4-(tetrahydro-2-furoyl) piperazine are suspended in a mixture made by 80 ml of methanol and 150 ml of acetone in a three-necked flask equipped with stirrer and cooling coil and the mixture is heated to the boiling temperature under strong stirring. An amount of 26.4 ml of a 7% (w/v) solution of hydrochloric acid in methanol is added during half an hour while keeping the mixture at the boiling temperature. The suspension is kept at the boiling temperature for another hour and half, then it is cooled to 20° C. under nitrogen atmosphere, then 1 ml of a 7% (w/v) solution of hydrochloric acid in methanol, is added kept under stirring for 15 minutes and finally filtered. The solid is washed on the filter with 20 ml of acetone and dried in oven under vacuum at 70° C. for 12 hours obtaining 19.7 g of product, having the same analytical characteristics as those of the product obtained in example 1, with a yield equal to 90.2%.

EXAMPLE 3

10 Grams of 1-(4-amino-6,7-dimethoxy-2-quinazolinyl)-4-(tetrahydro-2-furoyl) piperazine are suspended in a mixture made by 10 ml of methanol and 75 ml of n-butyl acetate in a three-necked flask equipped with stirrer and cooling coil and the mixture is heated to the boiling temperature under strong stirring. An amount of 9.2 ml of a 10% (w/v) solution of hydrochloric acid in methanol is added during the period of half an hour while keeping the mixture at the boiling temperature.

About 20 ml of mixture methanol/n-butyl acetate are distilled off 10 minutes after the end of the addition until the temperature of 95° C. is attained. Then the reaction mixture is cooled to 20° C. under nitrogen atmosphere, an amount of 0.3 ml of a 10% (w/v) solution of hydrochloric acid in methanol, is added kept under stirring for 10 minutes and then filtered. The solid is washed on the filter with 10 ml of n-butyl acetate and dried in oven under vacuum at 70° C. for 12 hours obtaining 10.8 g of product, having the same analytical characteristics as those of the product obtained in example 1, with a yield equal to 98.8%.

EXAMPLE 4

6 Kilograms of 1-(4-amino-6,7-dimethoxy-2-quinazolinyl)-4-(tetrahydro-2-furoyl) piperazine are suspended in a mixture made by 24 l of methanol and 45 l of n-butyl acetate in a reactor equipped with steam jacket, stirrer, cooling coil and tube for reagents introduction dipped under the level of the reaction mixture and the suspension is heated to 60° C. under strong stirring. An amount of 5.54 l of a 10% (w/v) solution of hydrochloric acid in methanol is added to the suspension during one hour and the mixture methanol/n-butyl acetate is partially distilled off 15 minutes after the end of the addition until the temperature of distillation arrives at 98° C. Subsequently the reaction mixture is cooled to 20° C. under nitrogen atmosphere, an amount of 0.32 l of a 10% (w/v) solution of hydrochloric acid in methanol is added and is filtered after 15 minutes of stirring. The solid is washed with 6 l of n-butyl acetate and dried in oven under vacuum at the temperature of 70° C. for 24 hours.

6.35 Kilograms of product are obtained, having the same analytical characteristics as those of the product obtained in example 1, with a yield equal to 96.7%.

EXAMPLE 5

20 Grams of 1-(4-amino-6,7-dimethoxy-2-quinazolinyl)-4-(tetrahydro-2-furoyl) piperazine are suspended in a mixture made by 80 ml of methanol and 150 ml of ethanol in a three-necked flask equipped with stirrer and cooling coil and the mixture is heated until 70° C. under strong stirring. An amount of 26.4 ml of a 7% (w/v) solution of hydrochloric acid in methanol is added to the suspension during the period of half an hour while keeping the temperature at 70° C.

The mixture methanol/ethanol is partially distilled off 10 minutes after the end of the addition while keeping the temperature at 70° C. for one hour. The reaction mixture is then cooled under nitrogen atmosphere till 20° C., then an amount of 1 ml of a 7% (w/v) solution of hydrochloric acid in methanol is added, kept under stirring for 15 minutes and finally filtered.

The solid is washed on the filter with 20 ml of ethanol and dried in oven under vacuum at 70° C. for 12 hours obtaining 20.3 g of product, having the same analytical characteristics as those of the product obtained in example 1, with a yield equal to 92.8%.

EXAMPLE 6

Example 5 is repeated by using isopropanol instead of ethanol. The only difference is that the temperature of distillation goes up 75° C. 21.2 Grams of product, having the same analytical characteristics as those of the product obtained in example 1, are obtained with a yield equal to 96.9%.

EXAMPLE 7

Example 5 is repeated by using n-butanol instead of ethanol. The only difference is that the temperature of distillation goes up 95° C. 21.1 Grams of product, having the same analytical characteristics as those of the product obtained in example 1, are obtained with a yield equal to 96.6%.

EXAMPLE 8

Example 5 is repeated by using methylisobutylketone instead of ethanol. The only difference is that the temperature of distillation goes up 93° C.

21.4 Grams of product, having the same analytical characteristics as those of the product obtained in example 1, are obtained with a yield equal to 97.8%.

We claim:

1. A process for the production of form I of anhydrous 1-(4-amino-6,7-dimethoxy-2-quinazolinyl)-4-(tetrahydro-2-furoyl)piperazine monohydrochloride which comprises the steps of:

(a) heating at a temperature between 50° C. and the boiling temperature a suspension of 1-(4-amino-6,7-dimethoxy-2-quinazolinyl)-4-(tetrahydro-2-furoyl)piperazine in a mixture made of methanol and a solvent which is a member selected from the group consisting of $C_2$ to $C_6$ straight or branched alcohols, esters of the $C_1$ to $C_8$ aliphatic carboxylic acids with straight or branched $C_1$ to $C_8$ alcohols, $C_3$ to $C_8$ aliphatic ketones, $C_4$ to $C_8$ straight, branched or cyclic aliphatic ethers, aliphatic amides and aliphatic nitriles;

(b) adding to said suspension under strong stirring in a period of time between 15 minutes and 2 hours from 0.95 to 1.00 equivalents of hydrochloric acid dissolved in methanol, while keeping the temperature between 50° C. and the boiling temperature;

(c) continuously heating at the boiling temperature for a period of time between 10 minutes and 3 hours;

(d) cooling the suspension to 20° C. under a nitrogen atmosphere;

(e) adding an amount of 0.02 to 0.10 equivalents of hydrochloric acid with respect to said suspension of said 1-(4-amino-6,7-dimethoxy-2-quinazolinyl)-4-(tetrahydro-2-furoyl)piperazine, said hydrochloric acid being dissolved in methanol while keeping the suspension under strong stirring for a period of time between 10 and 30 minutes, filtering said suspension, washing the solid with the solvent and drying it in an oven under vacuum at a temperature between 70° C. and 75° C. for a period of time between 12 and 24 hours.

2. The process according to claim 1 wherein in said step c), said mixture of methanol and solvent is partially distilled off.

3. The process according to claim 1 wherein said solvent is a member selected from the group consisting of ethanol, isopropanol, n-butanol, n-butyl acetate, acetone, methyl-isobutylketone and n-dibutylether and the mixture with methanol is made by an amount by volume of methanol between 1 and 8 times and by an amount by volume of said solvent between 3 and 15 times with respect of the weight of the 1-(4-amino-6,7-dimethoxy-2-quinazolinyl)-4-(tetrahydro-2furoyl)piperazine.

* * * * *